(12) United States Patent
Lang et al.

(10) Patent No.: US 12,262,921 B2
(45) Date of Patent: Apr. 1, 2025

(54) MODULAR HEAD ASSEMBLY

(71) Applicant: K2M, Inc., Leesburg, VA (US)

(72) Inventors: Brittany Lang, Warrenton, VA (US);
Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 18/011,612

(22) PCT Filed: Jun. 25, 2021

(86) PCT No.: PCT/US2021/039063
§ 371 (c)(1),
(2) Date: Dec. 20, 2022

(87) PCT Pub. No.: WO2021/263088
PCT Pub. Date: Dec. 30, 2021

(65) Prior Publication Data
US 2023/0233233 A1    Jul. 27, 2023

Related U.S. Application Data

(60) Provisional application No. 63/044,575, filed on Jun. 26, 2020.

(51) Int. Cl.
*A61B 17/70*    (2006.01)
*A61B 17/56*    (2006.01)

(52) U.S. Cl.
CPC ...... *A61B 17/7037* (2013.01); *A61B 17/7032* (2013.01); *A61B 2017/564* (2013.01)

(58) Field of Classification Search
CPC ............ A61B 17/7032; A61B 17/7035; A61B 17/7037
See application file for complete search history.

(56) References Cited

U.S. PATENT DOCUMENTS

| 856,265 A | 6/1907 | Kunkle |
| 5,382,248 A | 1/1995 | Jacobson et al. |
| (Continued) | | |

FOREIGN PATENT DOCUMENTS

| EP | 2873383 A1 | 5/2015 |
| WO | 2018023030 A1 | 2/2018 |
| WO | 2020056385 A1 | 3/2020 |

OTHER PUBLICATIONS

International Search Report for PCT/US2021/039063 dated Oct. 13, 2021. (2 pages).

(Continued)

*Primary Examiner* — Eduardo C Robert
*Assistant Examiner* — Michelle C Green
(74) *Attorney, Agent, or Firm* — Lerner David LLP (57) ABSTRACT

A spinal fixation device includes a modular head assembly and a bone screw having a head and a shank. The modular head assembly includes a housing defining proximal and distal surfaces and a throughhole therethrough; an anvil slidable within the throughhole; a biasing member circumferentially surrounding the anvil; an assembly cap secured to the housing and defining an inner surface having a first portion with a first diameter and a second portion with a second diameter smaller than the first diameter; a retaining ring movable from the first portion of the assembly cap to the second portion of the assembly cap to transition the retaining ring between a first configuration in which the retaining ring is sized to receive the head of the bone screw and a second configuration in which the retaining ring is compressed about the bone screw to fix the bone screw relative to the modular head assembly.

20 Claims, 9 Drawing Sheets

(56) References Cited

U.S. PATENT DOCUMENTS

| | | |
|---|---|---|
| 5,487,744 A | 1/1996 | Howland |
| 5,549,608 A | 8/1996 | Errico et al. |
| 5,554,157 A | 9/1996 | Errico et al. |
| 5,575,972 A | 11/1996 | Mitsuhashi et al. |
| 5,578,033 A | 11/1996 | Errico et al. |
| 5,584,834 A | 12/1996 | Errico et al. |
| 5,586,984 A | 12/1996 | Errico et al. |
| 5,609,593 A | 3/1997 | Errico et al. |
| 5,609,594 A | 3/1997 | Errico et al. |
| 5,669,911 A | 9/1997 | Errico et al. |
| 5,725,528 A | 3/1998 | Errico et al. |
| 5,733,285 A | 3/1998 | Errico et al. |
| 5,735,851 A | 4/1998 | Errico et al. |
| 5,800,435 A | 9/1998 | Errico et al. |
| 5,817,094 A | 10/1998 | Errico et al. |
| 6,004,322 A | 12/1999 | Bernstein |
| 6,050,997 A | 4/2000 | Mullane |
| 6,146,383 A | 11/2000 | Studer et al. |
| 6,280,442 B1 | 8/2001 | Barker et al. |
| 6,482,207 B1 | 11/2002 | Errico |
| 6,623,485 B2 | 9/2003 | Doubler et al. |
| 6,660,004 B2 | 12/2003 | Barker et al. |
| 6,669,697 B1 | 12/2003 | Pisharodi |
| 6,733,502 B2 | 5/2004 | Altarac et al. |
| 6,837,889 B2 | 1/2005 | Shluzas |
| 6,869,433 B2 | 3/2005 | Glascott |
| 6,887,242 B2 | 5/2005 | Doubler et al. |
| 7,066,937 B2 | 6/2006 | Shluzas |
| 7,087,057 B2 | 8/2006 | Konieczynski et al. |
| 7,144,396 B2 | 12/2006 | Shluzas |
| 7,186,255 B2 | 3/2007 | Baynham et al. |
| 7,306,606 B2 | 12/2007 | Sasing |
| 7,314,467 B2 | 1/2008 | Howland |
| 7,322,981 B2 | 1/2008 | Jackson |
| 7,662,175 B2 | 2/2010 | Jackson |
| 7,682,377 B2 | 3/2010 | Konieczynski et al. |
| 7,722,645 B2 | 5/2010 | Bryan |
| 7,727,261 B2 | 6/2010 | Barker et al. |
| 7,749,258 B2 | 7/2010 | Biedermann et al. |
| 7,766,943 B1 | 8/2010 | Fallin et al. |
| 7,766,945 B2 | 8/2010 | Nilsson et al. |
| 7,776,067 B2 | 8/2010 | Jackson |
| 7,785,354 B2 | 8/2010 | Biedermann et al. |
| 7,789,896 B2 | 9/2010 | Jackson |
| 7,833,250 B2 | 11/2010 | Jackson |
| 7,842,073 B2 | 11/2010 | Richelsoph et al. |
| 7,879,075 B2 | 2/2011 | Shluzas |
| 7,901,435 B2 | 3/2011 | Slivka et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,172 B2 | 5/2011 | Chao et al. |
| 7,951,173 B2 | 5/2011 | Hammill, Sr. et al. |
| 8,007,518 B2 | 8/2011 | Winslow et al. |
| 8,012,181 B2 | 9/2011 | Winslow et al. |
| 8,016,861 B2 | 9/2011 | Mitchell et al. |
| 8,048,115 B2 | 11/2011 | Winslow et al. |
| 8,048,126 B2 | 11/2011 | Altarac et al. |
| 8,048,133 B2 | 11/2011 | Biedermann et al. |
| 8,052,724 B2 | 11/2011 | Jackson |
| 8,057,515 B2 | 11/2011 | Flynn et al. |
| 8,057,519 B2 | 11/2011 | Justis et al. |
| 8,066,744 B2 | 11/2011 | Justis et al. |
| 8,075,603 B2 | 12/2011 | Hammill, Sr. et al. |
| 8,083,772 B2 | 12/2011 | Winslow et al. |
| 8,083,775 B2 | 12/2011 | Winslow et al. |
| 8,083,777 B2 | 12/2011 | Butters et al. |
| 8,088,152 B2 | 1/2012 | Schumacher |
| 8,092,501 B2 | 1/2012 | Mitchell et al. |
| 8,092,504 B2 | 1/2012 | Warnick |
| 8,097,024 B2 | 1/2012 | Winslow et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,133,262 B2 | 3/2012 | Whipple |
| 8,137,384 B2 | 3/2012 | Heiges et al. |
| 8,137,386 B2 | 3/2012 | Jackson |
| 8,142,481 B2 | 3/2012 | Warnick |
| 8,147,522 B2 | 4/2012 | Warnick |
| 8,167,912 B2 | 5/2012 | Jacofsky et al. |
| 8,172,876 B2 | 5/2012 | Janowski et al. |
| 8,192,468 B2 | 6/2012 | Biedermann et al. |
| 8,192,470 B2 | 6/2012 | Biedermann et al. |
| 8,197,518 B2 | 6/2012 | Hammill, Sr. et al. |
| 8,211,155 B2 | 7/2012 | Winslow et al. |
| 8,216,281 B2 | 7/2012 | Winslow et al. |
| 8,221,471 B2 | 7/2012 | Kovach et al. |
| 8,257,397 B2 | 9/2012 | Winslow et al. |
| 8,267,969 B2 | 9/2012 | Altarac et al. |
| 8,298,265 B2 | 10/2012 | Purcell et al. |
| 8,298,274 B2 | 10/2012 | Barker, Jr. et al. |
| 8,333,792 B2 | 12/2012 | Winslow et al. |
| 8,337,530 B2 | 12/2012 | Hestad et al. |
| 8,337,536 B2 | 12/2012 | Mitchell et al. |
| 8,372,122 B2 | 2/2013 | Winslow et al. |
| 8,394,127 B2 | 3/2013 | Winslow et al. |
| 8,398,689 B2 | 3/2013 | Abdou |
| 8,430,916 B1 | 4/2013 | Winslow et al. |
| 8,444,681 B2 | 5/2013 | Jackson et al. |
| 8,465,530 B2 | 6/2013 | Hammill, Sr. et al. |
| 8,475,501 B2 | 7/2013 | Jackson |
| 8,506,609 B2 | 8/2013 | Biedermann et al. |
| 8,506,611 B2 | 8/2013 | Biedermann et al. |
| 8,518,085 B2 | 8/2013 | Winslow et al. |
| 8,529,604 B2 | 9/2013 | Barker, Jr. et al. |
| 8,556,938 B2 | 10/2013 | Jackson et al. |
| 8,562,652 B2 | 10/2013 | Biedermann et al. |
| 8,617,217 B2 | 12/2013 | Iott et al. |
| 8,628,558 B2 | 1/2014 | Harvey et al. |
| 8,636,769 B2 | 1/2014 | Jackson |
| 8,636,781 B2 | 1/2014 | Biedermann et al. |
| 8,636,782 B2 | 1/2014 | Biedermann et al. |
| 8,663,288 B2 | 3/2014 | Konieczynski et al. |
| 8,663,290 B2 | 3/2014 | Doubler et al. |
| 8,663,291 B2 | 3/2014 | Doubler et al. |
| 8,685,064 B2 | 4/2014 | Hestad et al. |
| 8,709,050 B2 | 4/2014 | Shluzas |
| 8,758,410 B2 | 6/2014 | Heiges et al. |
| 8,764,810 B2 | 7/2014 | Biedermann et al. |
| 8,814,911 B2 | 8/2014 | Jackson |
| 8,845,700 B2 | 9/2014 | Kwak et al. |
| 8,870,927 B2 | 10/2014 | Matthis et al. |
| 8,881,358 B2 | 11/2014 | Biedermann et al. |
| 8,888,827 B2 | 11/2014 | Harper et al. |
| 8,900,270 B2 | 12/2014 | Fauth et al. |
| 8,900,272 B2 | 12/2014 | Jackson |
| 8,926,671 B2 | 1/2015 | Biedermann et al. |
| 8,940,024 B2 | 1/2015 | Biedermann et al. |
| 8,961,568 B2 | 2/2015 | McKinley et al. |
| 8,979,904 B2 | 3/2015 | Jackson et al. |
| 8,986,349 B1 | 3/2015 | German et al. |
| 8,992,579 B1 | 3/2015 | Gustine et al. |
| 8,998,958 B2 | 4/2015 | Dauster et al. |
| 8,998,959 B2 | 4/2015 | Jackson et al. |
| 8,998,960 B2 | 4/2015 | Jackson |
| 8,998,967 B2 | 4/2015 | Biedermann et al. |
| 9,005,259 B2 | 4/2015 | Biedermann et al. |
| 9,017,390 B2 | 4/2015 | Biedermann et al. |
| 9,023,086 B2 | 5/2015 | Biedermann et al. |
| 9,044,273 B2 | 6/2015 | Richelsoph et al. |
| 9,060,814 B2 | 6/2015 | Doubler et al. |
| 9,066,759 B2 | 6/2015 | Biedermann et al. |
| 9,119,674 B2 | 9/2015 | Matthis et al. |
| 9,131,971 B2 | 9/2015 | Biedermann et al. |
| 9,144,444 B2 | 9/2015 | Jackson |
| 9,155,567 B2 | 10/2015 | Auerbach et al. |
| 9,173,684 B2 | 11/2015 | Biedermann et al. |
| 9,186,187 B2 | 11/2015 | Mishra |
| 9,198,694 B2 | 12/2015 | Mishra et al. |
| 9,198,695 B2 | 12/2015 | Shluzas et al. |
| 9,232,969 B2 | 1/2016 | Farris |
| 9,247,965 B2 | 2/2016 | Biedermann et al. |
| 9,254,150 B2 | 2/2016 | Biedermann et al. |

(56) References Cited

U.S. PATENT DOCUMENTS

| | | |
|---|---|---|
| 9,277,938 B2 | 3/2016 | Biedermann et al. |
| 9,277,941 B2 | 3/2016 | Biedermann et al. |
| 9,277,942 B2 | 3/2016 | Biedermann et al. |
| 9,289,244 B2 | 3/2016 | Hestad et al. |
| 9,289,246 B2 | 3/2016 | Biedermann et al. |
| 9,333,016 B2 | 5/2016 | Biedermann et al. |
| 9,333,017 B2 | 5/2016 | Biedermann et al. |
| 9,339,304 B2 | 5/2016 | Biedermann et al. |
| 9,339,320 B2 | 5/2016 | Heiges et al. |
| 9,351,766 B2 | 5/2016 | Biedermann et al. |
| 9,358,047 B2 | 6/2016 | Mishra et al. |
| 9,364,266 B2 | 6/2016 | Biedermann et al. |
| 9,439,680 B2 | 9/2016 | Biedermann et al. |
| 9,451,990 B2 | 9/2016 | Fauth et al. |
| 9,451,991 B2 | 9/2016 | Raju et al. |
| 9,452,006 B2 | 9/2016 | Biedermann et al. |
| 9,453,526 B2 | 9/2016 | Black et al. |
| 9,463,047 B2 | 10/2016 | Raju et al. |
| 9,463,049 B2 | 10/2016 | Konieczynski et al. |
| 9,480,517 B2 | 11/2016 | Jackson et al. |
| 9,486,245 B2 | 11/2016 | Matthis et al. |
| 9,486,246 B2 | 11/2016 | Biedermann et al. |
| 9,492,204 B2 | 11/2016 | Biedermann et al. |
| 9,510,868 B2 | 12/2016 | Biedermann et al. |
| 9,522,021 B2 | 12/2016 | Jackson et al. |
| 9,532,809 B2 | 1/2017 | Biedermann et al. |
| 9,532,810 B2 | 1/2017 | Hestad et al. |
| 9,549,763 B2 | 1/2017 | Harper et al. |
| 9,572,600 B2 | 2/2017 | Biedermann et al. |
| 9,579,125 B2 | 2/2017 | Raju et al. |
| 9,597,119 B2 | 3/2017 | Jackson et al. |
| 9,603,630 B2 | 3/2017 | Farris |
| 9,603,635 B2 | 3/2017 | Leff et al. |
| 9,615,858 B2 | 4/2017 | Doubler et al. |
| 9,649,139 B2 | 5/2017 | Sharifi-Mehr et al. |
| 9,649,142 B2 | 5/2017 | Doubler et al. |
| 9,693,808 B2 | 7/2017 | Fauth et al. |
| 9,707,013 B2 | 7/2017 | Rezach et al. |
| 9,737,338 B2 | 8/2017 | Bazille |
| 9,763,700 B1 | 9/2017 | Gregory |
| 9,788,865 B2 | 10/2017 | Matthis et al. |
| 9,820,780 B2 | 11/2017 | Duncan et al. |
| 9,839,446 B2 | 12/2017 | Biedermann et al. |
| 9,848,916 B2 | 12/2017 | Biedermann et al. |
| 9,883,892 B2 | 2/2018 | Jackson et al. |
| 9,895,170 B2 | 2/2018 | Biedermann et al. |
| 9,895,171 B2 | 2/2018 | Webb |
| 9,907,574 B2 | 3/2018 | Jackson et al. |
| 9,918,745 B2 | 3/2018 | Jackson et al. |
| 9,924,971 B2 | 3/2018 | Biedermann et al. |
| 9,924,975 B2 | 3/2018 | Jackson et al. |
| 9,936,983 B2 | 4/2018 | Mesiwala et al. |
| 9,949,763 B2 | 4/2018 | Rezach |
| 9,949,765 B2 | 4/2018 | Nichols et al. |
| 9,956,003 B2 | 5/2018 | Prevost |
| 9,956,006 B2 | 5/2018 | Jackson |
| 9,962,193 B2 | 5/2018 | Biedermann et al. |
| 9,980,753 B2 | 5/2018 | Jackson et al. |
| 10,022,158 B2 | 7/2018 | Biedermann et al. |
| 10,058,367 B2 | 8/2018 | Biedermann et al. |
| 10,064,659 B2 | 9/2018 | Biedermann et al. |
| 10,076,363 B2 | 9/2018 | Biedermann et al. |
| 10,130,395 B2 | 11/2018 | Leff et al. |
| 10,136,924 B2 | 11/2018 | Konieczynski et al. |
| 10,159,519 B2 | 12/2018 | Biedermann et al. |
| 10,182,848 B2 | 1/2019 | Biedermann et al. |
| 10,188,432 B2 | 1/2019 | Jackson et al. |
| 10,238,430 B2 | 3/2019 | Jackson et al. |
| 10,258,383 B2 | 4/2019 | Biedermann et al. |
| 10,258,384 B2 | 4/2019 | Gregory |
| 10,335,204 B2 | 7/2019 | Matthis et al. |
| 10,357,287 B2 | 7/2019 | Schlaepfer et al. |
| 10,363,073 B2 | 7/2019 | Raina et al. |
| 10,368,916 B2 | 8/2019 | May |
| 10,383,662 B2 | 8/2019 | Biedermann et al. |
| 10,478,229 B2 | 11/2019 | Jackson et al. |
| 10,568,667 B2 | 2/2020 | Biester et al. |
| 10,716,609 B2 | 7/2020 | Biedermann et al. |
| 10,722,272 B2 | 7/2020 | Biedermann et al. |
| 10,729,483 B2 | 8/2020 | Biedermann et al. |
| 10,779,862 B2 | 9/2020 | Biedermann et al. |
| 10,799,272 B2 | 10/2020 | Jackson |
| 10,813,672 B2 | 10/2020 | Jackson et al. |
| 10,856,909 B2 | 12/2020 | Jackson et al. |
| 10,856,911 B2 | 12/2020 | Jackson et al. |
| 10,869,694 B2 | 12/2020 | Jackson et al. |
| 10,918,420 B2 | 2/2021 | Jackson et al. |
| 10,945,768 B2 | 3/2021 | Jackson et al. |
| 10,966,759 B2 | 4/2021 | Gregory |
| 10,980,574 B2 | 4/2021 | Konieczynski et al. |
| 10,987,137 B2 | 4/2021 | Jackson et al. |
| 11,020,150 B1 | 6/2021 | Doubler et al. |
| 11,090,090 B2 | 8/2021 | Biedermann et al. |
| 11,123,109 B2 | 9/2021 | Biedermann et al. |
| 11,147,597 B2 | 10/2021 | Jackson |
| 11,160,582 B2 | 11/2021 | Biedermann et al. |
| 11,219,470 B2 | 1/2022 | Avidano et al. |
| 2003/0060823 A1 | 3/2003 | Bryan |
| 2004/0097933 A1 | 5/2004 | Lourdel et al. |
| 2006/0200131 A1 | 9/2006 | Chao et al. |
| 2007/0088357 A1* | 4/2007 | Johnson ............ A61B 17/7037 606/86 A |
| 2007/0090238 A1 | 4/2007 | Justis |
| 2008/0262556 A1 | 10/2008 | Jacofsky et al. |
| 2010/0125302 A1 | 5/2010 | Hammill, Sr. et al. |
| 2010/0137920 A1 | 6/2010 | Hammill, Sr. et al. |
| 2010/0198272 A1 | 8/2010 | Keyer et al. |
| 2010/0305621 A1 | 12/2010 | Wang et al. |
| 2011/0118783 A1 | 5/2011 | Winslow et al. |
| 2011/0307018 A1 | 12/2011 | Zucherman et al. |
| 2012/0041490 A1 | 2/2012 | Jacob et al. |
| 2013/0012954 A1 | 1/2013 | Paroth et al. |
| 2013/0046345 A1 | 2/2013 | Jones et al. |
| 2013/0110180 A1 | 5/2013 | Doubler et al. |
| 2013/0150852 A1* | 6/2013 | Shluzas .................. A61B 17/70 606/65 |
| 2014/0046374 A1 | 2/2014 | Asaad et al. |
| 2014/0257411 A1* | 9/2014 | Rezach ............ A61B 17/7037 606/305 |
| 2014/0343617 A1 | 11/2014 | Hannen |
| 2015/0196337 A1 | 7/2015 | Biedermann et al. |
| 2015/0196338 A1 | 7/2015 | Biedermann et al. |
| 2015/0201972 A1* | 7/2015 | Doubler ............ A61B 17/7002 606/266 |
| 2015/0250512 A1* | 9/2015 | Poker ................ A61B 17/7037 606/305 |
| 2015/0282844 A1* | 10/2015 | Vedula ............... A61B 17/8625 606/305 |
| 2016/0030086 A1 | 2/2016 | Mishra |
| 2016/0030090 A1 | 2/2016 | Webb |
| 2016/0220277 A1 | 8/2016 | Rezach et al. |
| 2016/0262801 A1 | 9/2016 | Rezach et al. |
| 2017/0020574 A1 | 1/2017 | Biedermann et al. |
| 2017/0049482 A1 | 2/2017 | Campbell et al. |
| 2017/0049484 A1 | 2/2017 | Leff et al. |
| 2017/0065306 A1 | 3/2017 | Fauth et al. |
| 2017/0112542 A1 | 4/2017 | Biedermann et al. |
| 2017/0172630 A1 | 6/2017 | Biedermann et al. |
| 2017/0224386 A1 | 8/2017 | Leff et al. |
| 2017/0245898 A1 | 8/2017 | May et al. |
| 2017/0265903 A1 | 9/2017 | Longtain et al. |
| 2017/0333085 A1 | 11/2017 | Jackson et al. |
| 2018/0014858 A1 | 1/2018 | Biester et al. |
| 2018/0014862 A1 | 1/2018 | Raina et al. |
| 2018/0014863 A1 | 1/2018 | Biester et al. |
| 2018/0021068 A1 | 1/2018 | May et al. |
| 2018/0036039 A1 | 2/2018 | Biedermann et al. |
| 2018/0055545 A1 | 3/2018 | Biedermann et al. |
| 2018/0092679 A1 | 4/2018 | Toon et al. |
| 2018/0110548 A1 | 4/2018 | May et al. |
| 2018/0116696 A1* | 5/2018 | Hammer ............ A61B 17/7056 |
| 2019/0110817 A1 | 4/2019 | Shluzas et al. |

(56) References Cited

U.S. PATENT DOCUMENTS

2019/0150989 A1  5/2019 Biester et al.
2020/0038075 A1* 2/2020 Barrus ............... A61B 17/7091

OTHER PUBLICATIONS

International Search Report issued in Appln. No. PCT/US2021/059376 mailed Feb. 3, 2022 (2 pages).
European Search Report issued in Appln. No. 21217539.2 dated Jun. 10, 2022 (2 pages).
International Search Report issued in Appln. No. PCT/US2022/039395 mailed Jan. 31, 2023 (4 pages).
Extended European Search Report including Search Opinion from 21828986.6, dated Jun. 14, 2024, pp. 1-5.

* cited by examiner

MODULAR HEAD ASSEMBLY

CROSS REFERENCE TO RELATED APPLICATIONS

This application is a national phase entry under 35 U.S.C. § 371 of International Application No. PCT/US2021/039063, filed Jun. 25, 2021, published in English, which claims the benefit of the filing date of U.S. Provisional Patent Application No. 63/044,575 filed Jun. 26, 2020, entitled Modular Head Assembly, the disclosure of which is hereby incorporated herein by reference.

BACKGROUND OF THE INVENTION

The present disclosure relates to spinal fixation devices and, more particularly, to modular pedicle fixation assemblies.

The spinal column is a complex system of bones and connective tissues that provides support for the body while protecting the spinal cord and nerves. The spinal column includes a series of vertebral bodies stacked on top of one another, each vertebral body including an inner or central portion of relatively weak cancellous bone and an outer portion of relatively strong cortical bone. Situated between each vertebral body is an intervertebral disc that cushions and dampens compressive forces exerted upon the spinal column, as well as maintains proper spacing of the bodies with respect to each other. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine) and spondylolisthesis (forward displacement of one vertebra over another, usually in a lumbar or cervical spine), for example, that are caused by abnormalities, such as disease or trauma, and that are characterized by misalignment of the spinal column. When the spinal column is misaligned, one or more of the misaligned vertebral bodies can "pinch" or apply pressure to the underlying spinal cord and nerves, which often results in debilitating pain and diminished nerve function. For this reason, the forgoing conditions regularly require the imposition and/or maintenance of corrective forces on the spine in order to return the spine to its normal alignment.

A surgical technique, commonly referred to as spinal fixation, utilizes surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column.

One common type of spinal fixation device utilizes spinal rods placed generally parallel to the spine and fixation devices, such as pedicle screw assemblies, interconnected between the spinal rods and selected portions of the spine. In some instances, the spinal rods can then be connected to each other via cross-connecting members to provide a more rigid support and alignment system.

Pedicle screw assemblies typically include a bone screw and a housing or coupling element for coupling the bone screw to the spinal rod. Conventional pedicle screws are "top loaded" meaning that assembly of the pedicle screw requires inserting a shank of the bone screw into a proximal end of the housing until the head of the bone screw is retained within the housing and the shank extends from a distal end of the housing. Thus, when securing a conventional pedicle screw to bone, the surgeon must thread the screw into bone while the head of the screw is positioned within the housing.

Despite the improvements that have been made to spinal fixation devices, various drawbacks remain. For example, the housing of a conventional "top loaded" pedicle screw assembly can obstruct a surgeon's vision and/or access while performing operative tasks such as decortication and decompression. This problem is exacerbated by the fact that the housing is subject to "flop" (e.g., unwanted movement) around the head of the screw, which can complicate handling of the pedicle screw assembly, alignment of the housing and fastening of the pedicle screw assembly to bone.

BRIEF SUMMARY OF THE INVENTION

A "bottom loaded" or "modular" pedicle screw assembly is provided herein. Among other advantages, the distal end of the modular head assembly is configured to receive the head of the bone screw after the screw has been secured to bone. As a result, the surgeon's vision and access is not impaired while performing necessary operative tasks. Moreover, the modular head assembly includes a biasing member, such as a wave spring, that provides a constant biasing force to the head of the bone screw after the bone screw has been loaded through the bottom of the modular head assembly. The biasing force prevents the housing from "flopping" about the head of the screw, which improves intraoperative handling of the modular pedicle screw and alignment of the pedicle screw relative to the spinal rods and other components of the spinal fixation device.

One embodiment of the spinal fixation device includes a modular head assembly and a bone screw including a head and a shank extending from the head. The modular head assembly includes a housing defining a proximal surface, a distal surface and a throughhole formed therethrough; an anvil slidable within a portion of the throughhole; a biasing member circumferentially surrounding the anvil; an assembly cap secured to the housing including an inner surface defining a cavity having a first portion with a first diameter and a second portion with a second diameter smaller than the first diameter; a retaining ring positioned at least partially within the cavity and transitionable between a first configuration in which the retaining ring is sized to receive the head of the bone screw and a second configuration in which the retaining ring is compressed about the screw. Movement of the retaining ring from the first portion to the second portion compresses the retaining ring from the first configuration to the second configuration and secures the bone screw relative to the housing.

In another embodiment, a method of assembling a spinal fixation device is provided. The method includes: providing a modular head assembly including a housing having a throughhole formed through the housing from a proximal surface of the housing to a distal surface of the housing, an anvil slidable within a portion of the throughhole, a biasing member circumferentially surrounding the anvil, an assembly cap secured to the housing including an inner surface defining a cavity having a first portion with a first diameter and a second portion with a second diameter smaller than the first diameter, and a retaining ring positioned at least partially within the cavity of the assembly cap and transitionable between a first configuration in which the retaining ring is sized to receive a head of a bone screw and a second configuration in which the retaining ring is compressed about the bone screw; securing the bone screw within bone; positioning a bore defined through a distal surface of the assembly cap adjacent the head of the bone screw; advancing the modular head assembly over the head of the bone screw such that the head of the bone screw is received within the bore; moving the retaining ring from the second portion of the cavity to the first portion of the cavity; inserting the head of the bone screw through a lumen defined through distal and proximal surfaces of the retaining ring; and allowing the biasing member to apply a biasing force to the anvil which, in turn, applies a biasing force to the bone screw.

DETAILED DESCRIPTION

As used herein, when referring to the modular pedicle screw assembly, the term "proximal" means the portion of the assembly or a component thereof that is closer to the clinician and the term "distal" means the portion of the assembly or a component thereof that is furthest from the clinician. Also, as used herein, the terms "substantially," "generally," and "about" are intended to mean that slight deviations from absolute are included within the scope of the term so modified.

Figure 1A:
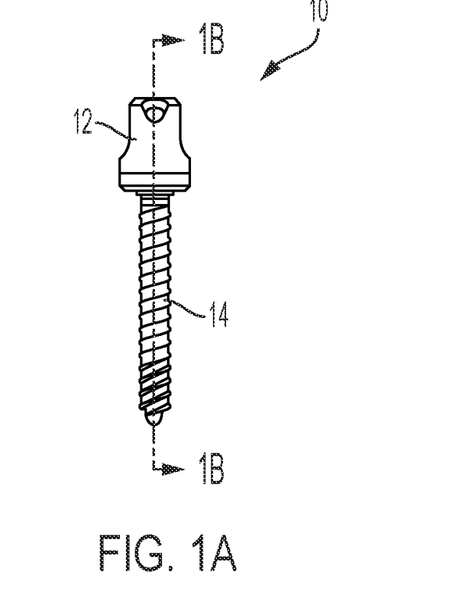
FIG. 1A is a side elevation view of a modular pedicle screw including a bone screw and modular head assembly according to an embodiment of the present disclosure.
Figure 1B:
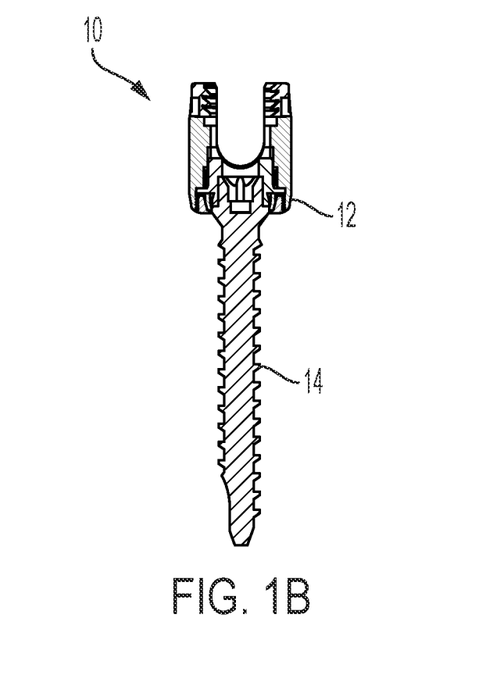
FIG. 1B is a cross section view of the modular pedicle screw of FIG. 1A taken along line 1B-1B.
Figure 1C:
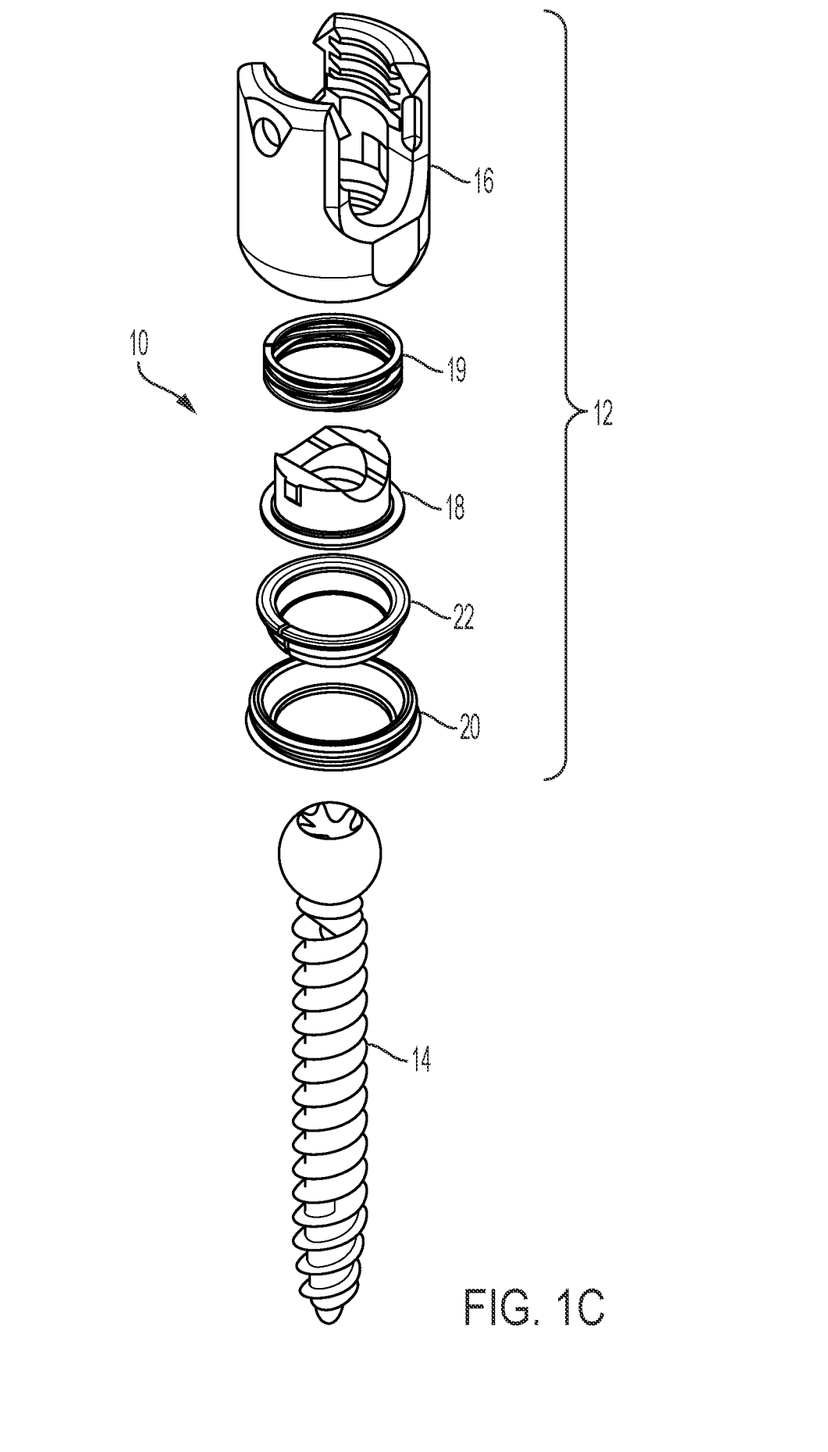
FIG. 1C is an exploded view of the pedicle screw of FIGS. 1A and 1B.

FIGS. 1A-1C illustrate a modular pedicle screw assembly 10 in accordance with an embodiment of the present disclosure. Pedicle screw 10 includes a modular head assembly 12 and a bone screw 14. Modular head assembly 12 is designed such that bone screw 14 can be "bottom loaded" or passed through a distal end of the modular head assembly and fastened to the bone screw after the screw has been implanted in bone.

With specific reference to FIG. 1C, modular head assembly 12 includes a housing 16, an anvil 18 slidable within a portion of the housing, a biasing member 19 circumferentially coupled about the anvil, a retaining ring 22 for fixing the rotational and angular position of the bone screw relative to the housing, and an assembly cap 20 for securing the anvil, the biasing member and the retaining ring within the housing. As is explained in further detail herein, after bone screw 14 has been loaded through the bottom of modular head assembly 12, biasing member 19 provides a constant biasing force to the head of the bone screw and prevents the modular head assembly from "flopping" relative to the bone screw.

Figure 2A:
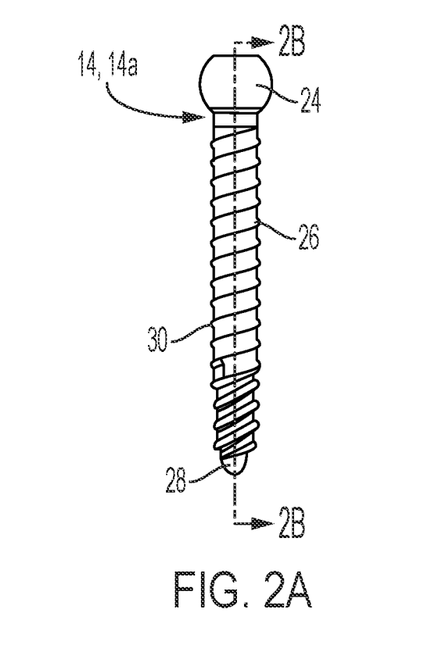
FIG. 2A is a side elevation view of a polyaxial bone screw of the pedicle screw of FIGS. 1A-1C.
Figure 2B:
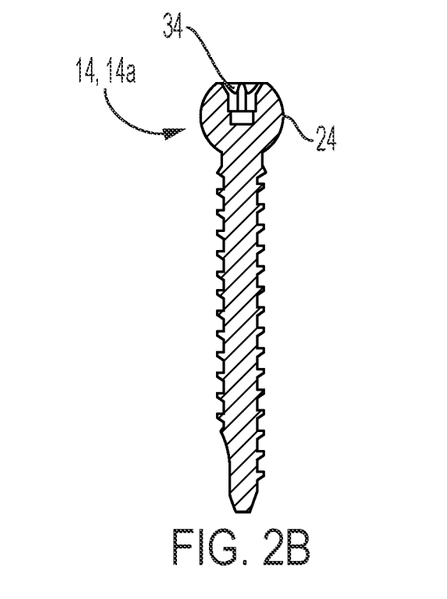
FIG. 2B is a cross section view of the bone screw of FIG. 2A taken along line 2B-2B.
Figure 2C:
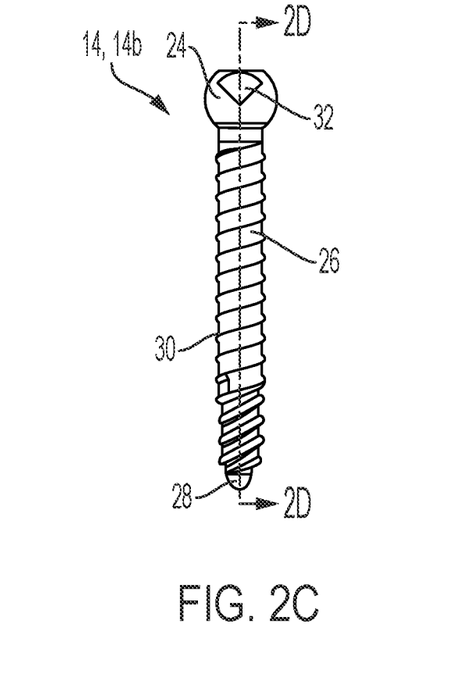
FIG. 2C is a side elevation view of uniplanar bone screw for use in the pedicle screw of FIGS. 1A-1C.
Figure 2D:
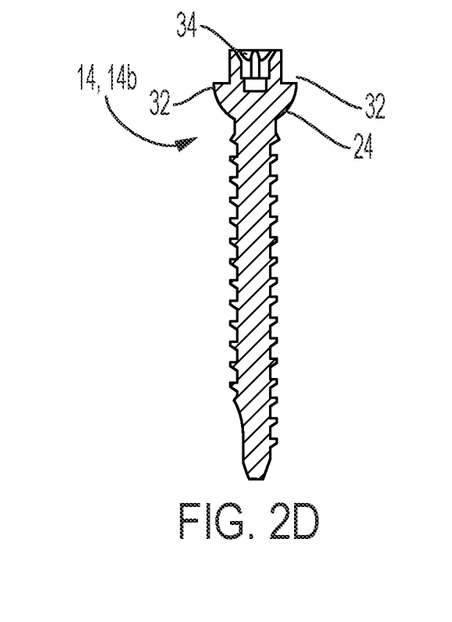
FIG. 2D is a cross section view of the bone screw of FIG. 2C taken along line 2D-2D.

Referring to FIGS. 2A-2D, bone screw 14 may be a polyaxial bone screw 14a (FIGS. 2A and 2B) or a uniplanar bone screw 14b (FIGS. 2C and 2D). Bone screw 14 includes a head 24 provided at a proximal end thereof and a shank 26 extending from the head along an axis. Shank 26 is formed as an elongated body and extends from a distal tip 28 to a proximal end that is coupled (e.g., monolithically formed) to head 24. Distal tip 28 is generally conically-shaped to facilitate insertion of the screw 14 into bone and, in some embodiments, may be self-starting. The elongated body of shank 26 may have a substantially uniform outer diameter upon which a helical thread 30 is provided that allows bone screw 14 to be threadably inserted and retained within bone. Helical thread 30 may be continuous or discontinuous, of uniform or non-uniform pitch, single threaded or double threaded and self-tapping or non-self-tapping depending upon the needs of the procedure being performed. It is also contemplated to include cutting flutes to facilitate implantation into bone. In some embodiments, bone screw 14 may be cannulated to permit the passage of a guide wire (not shown) or other instrumentation therethrough. In embodiments in which bone screw 14 defines a cannulation, it is contemplated that fenestrations (not shown) may be formed through an outer surface of shank 26 and into communication with the cannulation. Such a design may permit the introduction of bone cement or the like after implantation of the screw within bone.

As shown in FIGS. 2B and 2D, the head 24 of bone screw 14 defines a tool engaging recess 34 at a proximal portion thereof configured to receive a driving tool (not shown). Tool engaging recess 34 may be any suitable shape capable of transmitting a rotational motion of the tool to the head 24 of bone screw 14. In one non-limiting embodiment, tool engaging recess 34 may be a hexalobe, as described in U.S. Pat. No. 9,649,139, which is incorporated herein in reference in its entirety.

When the bone screw is a polyaxial bone screw 14a, the head 24 of the screw is generally spherical in shape which assists modular head assembly 12 in rotating in multiple axis relative to the bone screw. On the other hand, when the bone screw is a uniplanar bone screw 14b, the head 24 of the screw may define at least cutout 32 arranged to receive a corresponding feature(s), such as a protrusion(s), provided on a uniplanar anvil 18b (FIGS. 7A-7C) to restrict relative movement between modular head assembly 12 and the bone screw to a single plane. For example, the head 24 of uniplanar bone screw 14b may define a pair of cutouts 32 annularly spaced about the head of the bone screw. As shown in FIG. 2D, each cutout may form a surface that extends substantially parallel with a longitudinal axis of shaft 26. Thus, when the protrusions of uniplanar anvil 18b are positioned within the cutouts 32 of uniplanar bone screw 14b, the coaction between the protrusions and the corresponding flat surfaces restricts relative movement between modular head assembly 12 and the bone screw to a single plane.

Turning now to FIGS. 3A-3D, housing 16 has a generally cylindrical body with a proximal surface 36 and an opposite distal surface 38. Housing 16 defines a throughhole 40 extending along a longitudinal axis L of the body and between the proximal and distal surfaces of the housing.

Figure 3A:
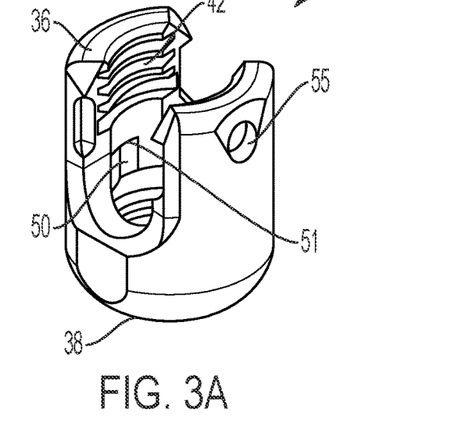
FIG. 3A is a perspective view of a housing of the pedicle screw of FIGS. 1A-1C.
Figure 3B:
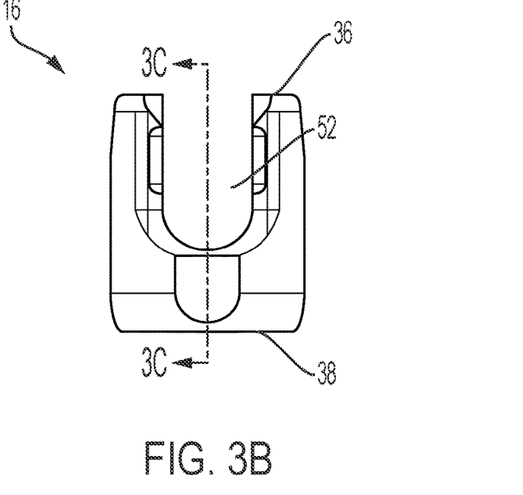
FIG. 3B is a side elevation view of the housing of FIG. 3A.
Figure 3C:
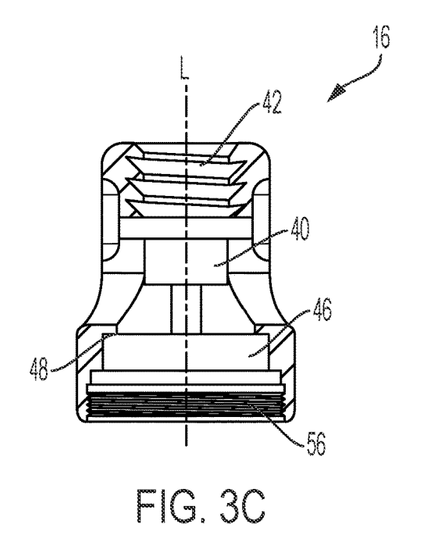
FIG. 3C is a cross section view of the housing of FIG. 3B taken along line 3C-3C.
Figure 3D:
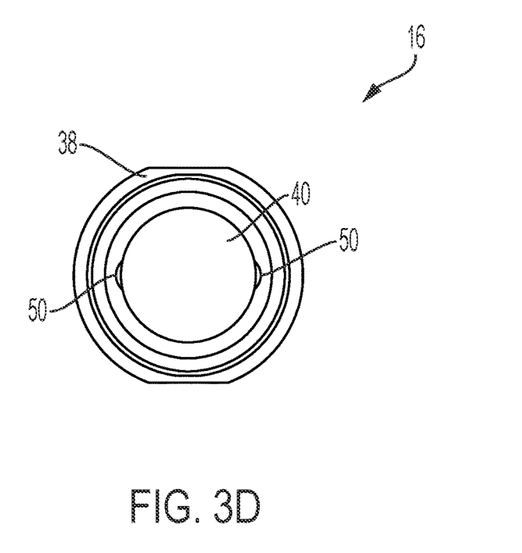
FIG. 3D is bottom elevation view of the housing of FIGS. 3A-3C.

The distal surface 38 of housing 16 defines a counterbore 46 that extends towards the proximal surface 36 of the housing and terminates at an annular face 48 located at a middle portion of the body, although it is contemplated that the counterbore may extend any suitable distance from the distal surface. As shown in FIGS. 3A and 3D, the sidewall delineating throughhole 40 defines a pair of longitudinally extending slots 50 in juxtaposed relationship to one another. Each slot 50 terminates at a stop 51 and is sized to receive a portion of anvil 18, thereby enabling the anvil to slidably translate along the length of the slot and inhibiting the anvil from rotating within throughhole 40. An inner sidewall, forming a distal portion of counterbore 46, defines an internal threading 56 for securing the assembly cap 20 to housing 16.

Figure 10A:
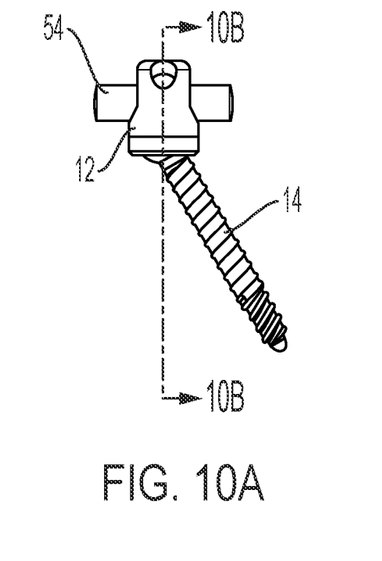
FIG. 10A is a side elevation view of an assembled spinal fixation device including a spinal rod, a set screw and the pedicle screw of FIGS. 1A-1C.
Figure 10B:
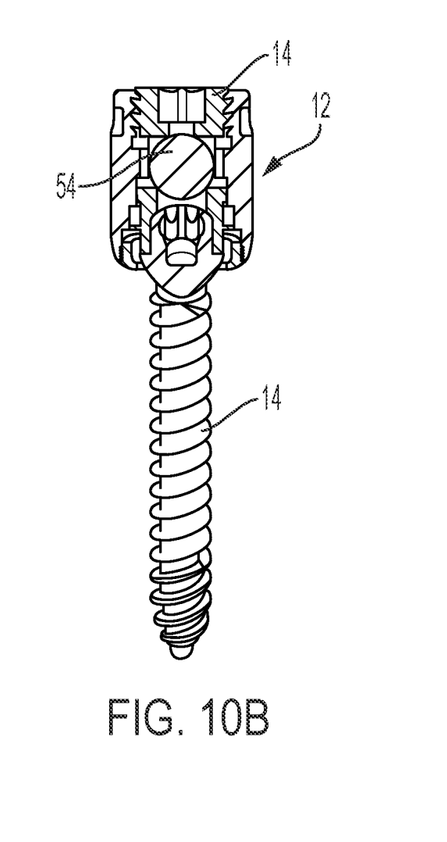
FIG. 10B is a cross section view of the spinal fixation device of FIG. 9A taken along line 10B-10B.

An outer surface of housing 16 defines a U-shaped opening 52 extending through the proximal surface 36 of the body in a transverse direction to throughhole 40. U-shaped opening 52 is sized and shaped to receive a spinal rod 54 (FIGS. 10A and 10B). As shown in FIGS. 3A and 3C, an inner sidewall delineating a proximal portion of throughhole 40 defines an internal threading 42 for threadably receiving a set screw 44 (FIG. 10B) and securing spinal rod 54 within the U-shaped opening 52 of housing 16. Two reliefs 55 are formed in the outer surface of housing 16. The reliefs 55 are configured to receive a suitable tool (not shown) and enable a clinician to grasp and manipulate housing 16 during a surgical procedure. Housing 16 may be formed from any biocompatible material suitable for use in surgical procedures, such as metallic materials including titanium, titanium alloys, stainless steels, cobalt chrome alloys, etc., or non-metallic materials such as ceramics, polyetheretherketone (PEEK), etc.

Figure 4A:
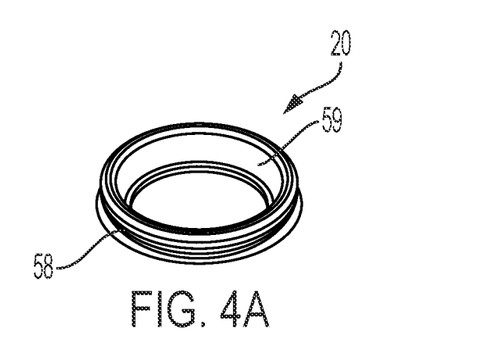
FIG. 4A is a perspective view of an assembly cap of the pedicle screw of FIGS. 1A-1C.
Figure 4B:
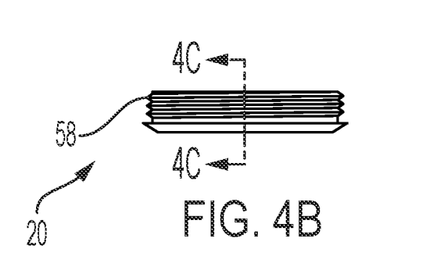
FIG. 4B is a side elevation view of the assembly cap of FIG. 4A.
Figure 4C:
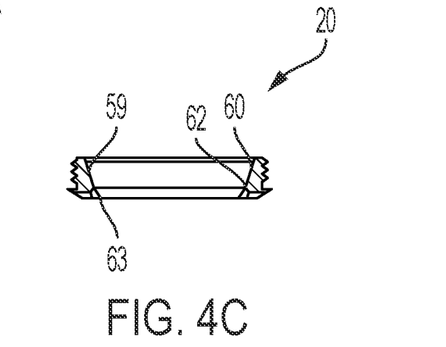
FIG. 4C is a cross section view of the assembly cap of FIG. 4B taken along line 4C-4C.

Assembly cap 20, shown in FIGS. 4A-4C, includes an external threading 58 configured to threadably engage the internal threading 56 of housing 16 to assemble modular head assembly 12. With specific reference to FIG. 4C, an interior surface of assembly cap 20 defines a cavity 59 for receiving retaining ring 22. The cavity 59 of assembly cap 20 is formed by an inwardly tapered sidewall extending from a proximal portion of the assembly cap to a distal portion of the assembly cap. Put differently, the cavity 59 of assembly cap 20 defines a first portion 60 (proximal portion) having a first diameter and a second portion 62 (distal portion) having a second diameter smaller than the first portion. As will be described in further detail hereinbelow, the cavity 59 of assembly cap 20 is thus sized to allow retaining ring 22 to expand as the retaining ring translates proximally from the second portion 62 of assembly cap 20 to the first portion 60 of the assembly cap. In contrast, as retaining ring 22 translates distally from the first portion 60 of assembly cap 20 to the second portion 62 of the assembly cap, the cavity 59 is sized to compress retaining ring 22. The distal end of assembly cap 20 may be provided with an inwardly projecting ledge 63 to limit the distal movement of retaining ring 22 and to prevent bone screw 14 from passing distally through modular head assembly 12 after the screw has been received therein.

Figure 5A:
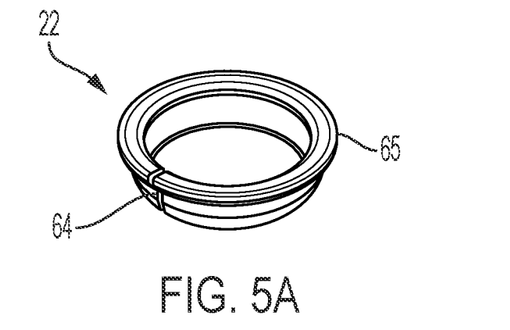
FIG. 5A is a perspective view of a retaining ring of the pedicle screw of FIGS. 1A-1C.
Figure 5B:
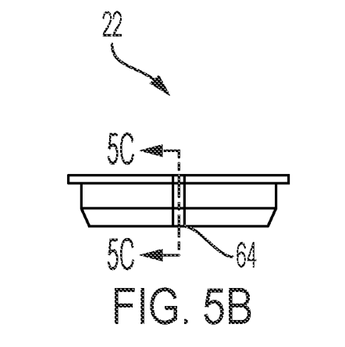
FIG. 5B is a side elevation view of the retaining ring of FIG. 5A.
Figure 5C:
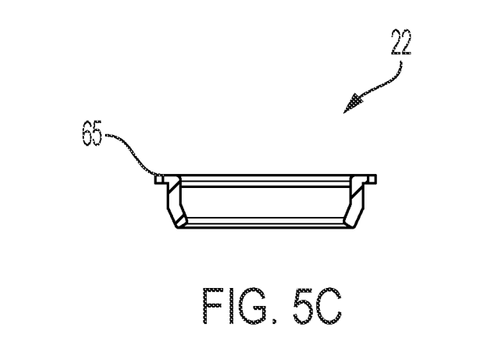
FIG. 5C is a cross section view of the retaining ring of FIG. 5B taken along line 5C-5C.

Referring to FIGS. 5A-5C, retaining ring 22 has a substantially ring shaped body sized to be slidably received within the cavity 59 of assembly cap 20 and a shelf 65 extending radially outward from a proximal end of the body. Shelf 65 has a relatively flat upper surface for engaging anvil 18 as retaining ring 22 translates within the cavity 59 of assembly cap 20. Retaining ring 22 is formed of an elastic material, such as an elastic metal, and defines a slit 64 extending therethrough from an outer surface of the ring shaped body to the inner surface of the body. In this manner, retaining ring 22 is configured to compress upon the application of an external force (e.g., a compressive force applied to an outer surface of the body) and to expand upon the application of an internal force (e.g., an expansion force applied to an inner surface of the cylindrical body). In this regard, retaining ring 22 is designed to transition between a neutral (or unexpanded configuration), an expanded configuration in which the retaining ring is sized to receive the head 24 of bone screw 14 and a compressed configuration in which the retaining ring prevents the head of the bone screw from passing distally through the retaining ring.

Figure 6A:
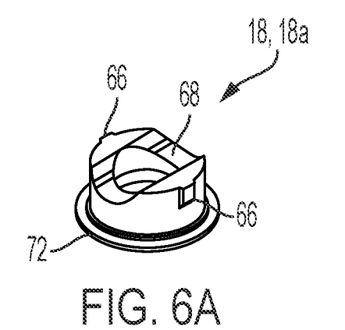
FIG. 6A is a perspective view of a polyaxial anvil of the pedicle screw of FIGS. 1A-1C.
Figure 6B:
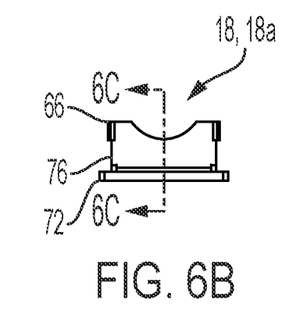
FIG. 6B is a side elevation view of the polyaxial anvil of FIG. 6A.
Figure 6C:
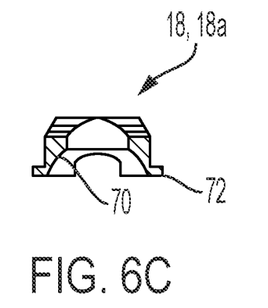
FIG. 6C is a cross section view of the polyaxial anvil of FIG. 6B taken along line 6C-6C.

As shown in FIGS. 6A-6C, polyaxial anvil 18a has a body defining a proximal surface 68, a distal surface 70 and an outer sidewall. The body of polyaxial anvil 18a is sized to slide within a portion of the throughhole 40 of housing 16. The proximal surface 68 of polyaxial anvil 18a defines a concave profile (e.g., extending toward the distal surface 70 of the body) configured to receive a portion of spinal rod 54 (FIGS. 10A and 10B). The outer surface of polyaxial anvil 18a includes a pair of lugs 66 diametrically opposed from one another about the body. Each one of the lugs 66 extends in the longitudinal direction and is sized to be received within a corresponding slot 50 of housing 16 to guide the sliding movement of polyaxial anvil 18a within throughhole 40 and to inhibit rotation of the anvil relative to the housing. In this manner, engagement between the lugs 66 of anvil 18a and the slots 50 of housing 16 ensure that the concave proximal surface of the anvil remains aligned with the U-shaped opening 52 of the housing to assist in properly aligning spinal rod 54 relative to modular head assembly 12.

The distal surface 70 of polyaxial anvil 18a defines a concave profile (e.g., extending toward the proximal surface 68 of the anvil). The concave profile of the distal surface 70 of polyaxial anvil 18a generally corresponds in shape to the spherical head 24 of polyaxial bone screw 14*a* thus allowing modular head assembly 12 to freely rotate in multiple directions about the head of the screw. Polyaxial anvil 18*a* includes an outwardly extending flange 72 circumscribing a distal end of the body. The combination of lugs 66 and flange 72 defines and annular seat 76 circumscribing the outer surface of polyaxial anvil 18*a*. The annular seat is arranged to receive biasing member 19 and to couple the biasing member to polyaxial anvil 18*a*. The bottom surface of flange 72 may be substantially flat and configured to engage the shelf 65 of retaining ring 22.

Figure 7A:
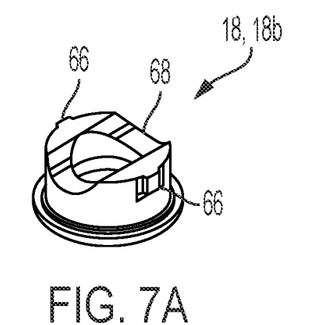
FIG. 7A is a perspective view of a uniplanar anvil of the pedicle screw of FIGS. 1A-1C.
Figure 7B:
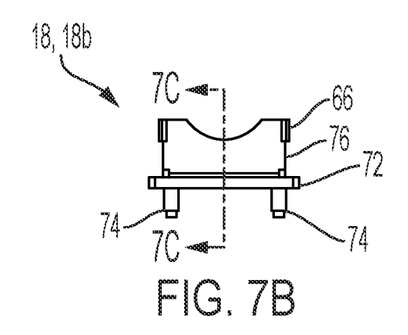
FIG. 7B is a side elevation view of the uniplanar anvil of FIG. 6A.
Figure 7C:
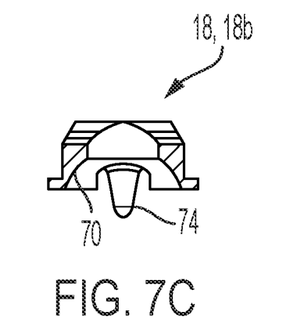
FIG. 7C is a cross section view of the uniplanar anvil of FIG. 6B taken along line 7C-7C.

Uniplanar anvil 18*b*, as shown in FIGS. 7A-7C, is substantially similar to polyaxial anvil 18*a* except that the uniplanar anvil additionally includes at least one protrusion 74. For example, uniplanar anvil 18*b* may include a pair of protrusions 74 extending from the distal surface 70 of the anvil in a longitudinal direction and to a location distal of flange 72. As shown in FIGS. 7B and 7C, protrusion 74 may be circumferentially spaced about the anvil 180 degrees from one another and aligned with a respective one of the lugs 66. Protrusions 74 are sized and shaped to be positioned within the cutout(s) 32 of uniplanar bone screw 14*b* and to engage with the substantially flat surface of the screw head. The cooperation between the protrusions 74 of uniplanar anvil 18*b* and the head 24 of uniplanar bone screw 14*b* restricts movement of modular head assembly 12 relative to the bone screw to a single plane (e.g., the midplane between the protrusions).

Figure 8:
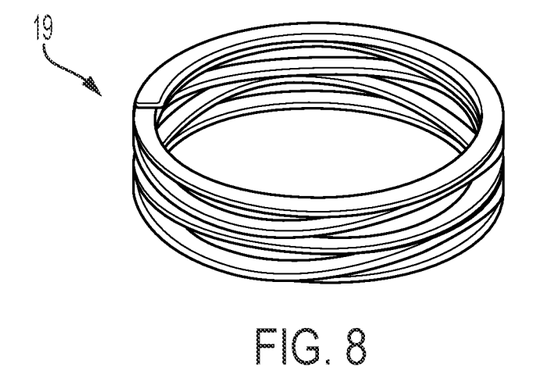
FIG. 8 is a perspective view of a wave spring of the pedicle screw of FIGS. 1A-1C.

As shown in FIG. 8, biasing member 19 may be a low profiled spring, such as a wave spring, configured to sit within the annular seat 76 of anvil 18 and to entirely circumscribe the outer surface of the anvil. In this regard, when modular head assembly 12 is assembled, the wave spring is positioned to engage the annular face 48 of counterbore 46 (FIG. 9B). As a result, when the head 24 of bone screw 14 is bottom loaded through retaining ring 22 and into engagement with anvil 18, the wave spring will impart a biasing force to the bone screw. This biasing force ensures that the distal surface 70 of anvil 18 applies a constant distally directed force against the head of the bone screw and prevents modular head assembly 12 from "flopping" loosely about the head of the bone screw. In this manner, the biasing force affords the clinician greater control while securing modular head assembly 12 to bone screw 24. Furthermore, because the wave spring is seated within the annular seat 76 of anvil 18 prior to inserting the anvil into housing 16, modular head assembly 12 can be quickly and, more accurately, assembled without requiring a user to align and load individual springs within a pocket of the housing and/or pocket of the anvil prior to inserting the anvil into the housing in separate and consecutive steps.

Figure 9A:
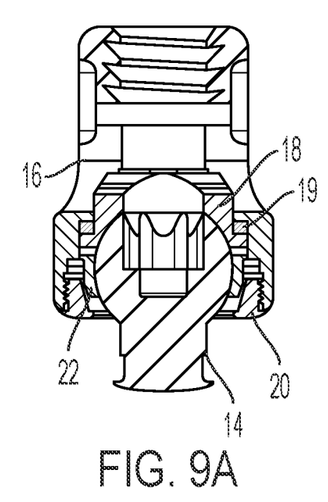
FIGS. 9A and 9B are cross section views illustrating the bone screw of FIGS. 2A-2B being bottom loaded into the modular head assembly of FIGS. 1A-1C.
Figure 9B:
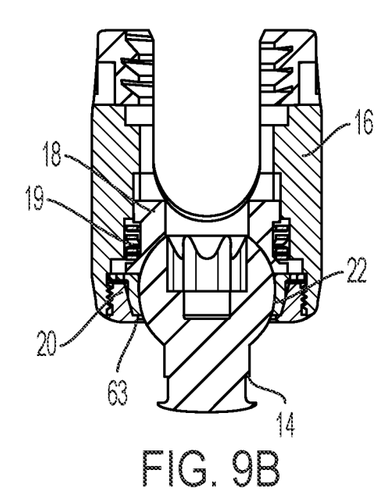

FIGS. 9A and 9B illustrate modular pedicle screw assembly 10 in an assembled state. Irrespective of whether modular head 12 encompasses a polyaxial bone screw 14*a* and a polyaxial anvil 18*a*, or a uniplanar bone screw 14*b* and a uniplanar anvil 18*b*, the modular head is assembled in the same manner. For this reason, the following description of the assembly process refers to the bone screw and the anvil generically as bone screw 14 and anvil 18.

Modular head 12 may be assembled by a manufacturer or an end user. To assembly modular head 12, spring 19 is first snapped over lugs 66, in a proximal to distal direction, and seated within the annular seat 76 of anvil 18. In this position, the spring may be slightly biased between lugs 66 and flange 72 which aids in securing the spring circumferentially about the outer surface of anvil 18. A user may then insert anvil 18 through the distal end 38 of housing 16 and position lugs 66 into the corresponding slots 50 of the before sliding the anvil proximally within throughhole 40 until spring 19 engages the annular face 48 of counterbore 46. Next, retaining ring 22 may be inserted into the cavity 59 of assembly cap 20. The external threading 58 of assembly cap 20 may then be threaded into the internal threading 56 of housing 16 to threadably secure the assembly cap to the housing and, in turn, to secure anvil 18, spring 19 and retaining ring 22 within the housing. It will be appreciated, however, that assembly cap 20 may be secured to housing 16 via welding or any other known coupling mechanism. In this regard, a manufacturer can assemble modular head 12 before shipping the modular head to the end user, or alternatively, an end user could assemble the modular head before surgery.

Use of pedicle screw assembly 10 to fixate spinal rod 54 will now be described. The surgeon may first evaluate the desired placement of spinal rod 54 and determine the desired type(s) of bone screws best suited for the operation. Because polyaxial anvil 18*a* is secured to polyaxial bone screw 14*a* in substantially the same manner in which uniplanar anvil 18*b* is secured to uniplanar bone screw 14*b*, a single generic description of the coupling will be described hereinafter such that specific descriptions pertaining to the polyaxial and uniplanar components are only set forth when describing contrasting features between the modular assemblies.

Bone screw 14 is first driven into bone using a driving tool (not shown) by inserting a working end of the driving tool into the tool engaging recess 34 of the head 24 and rotating the driving tool to thread the screw into bone. With the bone screw 14 secured at a desired location, modular head assembly 12 may be placed adjacent the head 24 of screw 14 and advanced in a distal direction over the head of the bone screw. As the head 24 of bone screw 14 is advanced proximally within throughhole 40, the head of the bone screw contacts retaining ring 22 and forces the retaining ring and anvil 18 in a proximal direction. More particularly, retaining ring 22 translates in a proximal direction from the distal portion 62 of assembly cap 20 into the proximal portion 60 of the assembly cap. The interaction of the lugs 66 of anvil 18 and the slots 50 of housing 16 guides proximal movement of the anvil within throughhole 40 until the proximal surface 68 of the anvil engages the stop 51 of the slot. With anvil 18 pressed against stop 51, continued application of a distally directed force on modular head assembly 12, will force the head 24 of bone screw 14 through retaining ring 22 and into contact with the concave, distal surface 70 of anvil 18. Specifically, the head 24 of bone screw 14 will place an outwardly directed force on an interior surface of retaining ring 22 and cause the elastic retaining ring to transition from a natural configuration to an expanded (e.g., larger diameter) configuration allowing the head of the bone screw to pass completely though the aperture of the retaining ring. It will be appreciated that retaining ring 22 is permitted to expand to the expanded configuration, in part, because the retaining ring is disposed within the larger, proximal portion 60 of the cavity 59 of assembly cap 20. Once the head 24 of bone screw 14 has completely passed through retaining ring 22, the retaining ring will elastically return to its natural size about the neck (e.g., the junction of the proximal portion of shank 26 and the head) of bone screw 14.

With specific reference to FIG. 9B, when modular head 12 is coupled to bone screw 14, the spring 19 of anvil 18 contact the annular face 48 of counterbore 46 and imparts a biasing force on the anvil which ensures that the distal surface 70 of the anvil applies a constant force to the head 24 of the bone screw. The constant force prevents modular head assembly 12 from "flopping" loosely about the head 24 of the screw 14. In this regard, the orientation and position of modular head assembly 12, relative to bone screw 14, is not altered unless the surgeon intentionally applies a meaningful rotational force to the modular head assembly. As a result, the biasing force affords the clinician greater control and the ability to make minor adjustments in the position of the modular head assembly relative to the screw.

If pedicle screw assembly 10 includes a polyaxial bone screw 14a and a polyaxial anvil 18a, the spherically shaped head 24 of the polyaxial bone screw will permit the concave distal surface 70 of the anvil to rotate about the head in multiple directions, thereby allowing the surgeon to adjust the position of modular head assembly 12 relative the bone screw in multiple axis. In contrast, if pedicle screw assembly 10 includes a uniplanar bone screw 14b and a uniplanar anvil 18b, the protrusions 74 of the uniplanar anvil will be positioned within cutouts 32 and engaged with the opposing flat surface of the head 24 of the uniplanar screw, thereby restricting the surgeon's ability to adjust modular head assembly 12 relative to the bone screw to a single axis.

Referring now to FIGS. 10A and 10B, spinal rod 54 may then be interconnected between adjacent modular head assemblies 12 by inserting the spinal rod within the U-shaped openings 52 of each housing 16 and within the concave relief of the proximal surface 68 of anvil 18. Again, the biasing force imparted by spring 19 will prevent modular head assemblies 12 from rotating relative to their bone screws 14 during placement of the spinal rod 54 (e.g., as a result of gravitations forces and/or minor forces imparted by the rod itself). In this regard, spring 19 assists in more efficiently and more accurately assembling the fixation device.

With spinal rod 54 properly positioned between modular head assemblies 12, the surgeon may then use a driving tool to thread set screw 44 into the threads 42 of housing 16, which in turn, forces the spinal rod, anvil 18 and retaining ring 22 to translate in a distal direction within the throughhole 40 of the housing. As retaining ring 22 moves in the distal direction, from the proximal portion 60 of cavity 59 to the distal portion 62 of the cavity, the inwardly tapered sidewall forming the cavity will impart an inwardly directed force on an outer surface of the retaining ring and cause the retaining ring to transition to the compressed configuration and clamp around the neck of bone screw 14, thereby fixing the rotational and angular position of the bone screw relative to housing 16 and preventing the bone screw from passing through a distal end of the housing.

To summarize the foregoing, a spinal fixation device includes a bone screw having a head and a shank extending from the head; and a modular head assembly that includes a housing having a proximal surface, a distal surface, and a throughhole formed through the housing from the proximal surface to the distal surface; an anvil slidable within a portion of the throughhole; a biasing member circumferentially surrounding the anvil; an assembly cap secured to the housing and including including an inner surface defining a cavity having a first portion with a first diameter and a second portion with a second diameter smaller than the first diameter; a retaining ring positioned at least partially within the cavity of the assembly cap and transitionable between a first configuration in which the retaining ring is sized to receive the head of the bone screw and a second configuration in which the retaining ring is compressed about the bone screw, whereby movement of the retaining ring from the first portion to the second portion compresses the retaining ring from the first configuration to the second configuration and secures the bone screw relative to the housing; and/or the distal portion of the housing may define a counterbore terminating at an annular face; and/or an inner surface of the housing may define at least one slot; and/or the anvil may defined a proximal end, a distal end and a circumferential sidewall extending therebetween, the circumferential sidewall may include at least one outwardly extending lug arranged to be slidably received within the at least one slot; and/or the at least one lug may include two lugs diametrically opposed from one another about the circumferential sidewall of the anvil; and/or the distal end of the anvil may include an outwardly extending flange; and/or the biasing member may be secured between the outwardly extending flange and the at least one outwardly extending lug; and/or the biasing member may be biased between the outwardly extending flange of the anvil and the annular face of the counterbore; and/or the biasing member may be a wave spring; and/or the counterbore may define an internal threading and the assembly cap may include an external threading configured to threadably engage the internal threading of the counterbore; and/or the retaining ring may define a proximal end and a distal end, the proximal and distal ends may define a lumen therethrough; and/or the retaining ring may be formed from a resilient material, and an outer surface of the retaining ring may define a slit in communication with the lumen; and/or the proximal end of the retaining ring may define an outwardly extending shelf arranged to contact the anvil; and/or the inner surface of the assembly cap may include an inwardly extending ledge at a distal end of the assembly cap to limit distal movement of the retaining ring.

A method of assembling a spinal fixation device includes: providing a modular head assembly, which includes housing having a throughhole formed through the housing from a proximal surface of the housing to a distal surface of the housing, an anvil slidable within a portion of the throughhole, a biasing member circumferentially surrounding the anvil, an assembly cap secured to the housing including an inner surface defining a cavity having a first portion with a first diameter and a second portion with a second diameter smaller than the first diameter, and a retaining ring positioned at least partially within the cavity of the assembly cap and transitionable between a first configuration in which the retaining ring is sized to receive a head of a bone screw and a second configuration in which the retaining ring is compressed about the bone screw; securing a bone screw within bone; positioning a bore defined through a distal surface of an assembly cap adjacent to the head of the bone screw; advancing the modular head assembly over the head of the bone screw such that the head of the bone screw is received within the bore; moving the retaining ring from the second portion of the cavity to the first portion of the cavity; inserting the head of the bone screw through a lumen defined through distal and proximal surfaces of the retaining ring; and allowing the biasing member to apply a biasing force to the anvil which, in turn, applies a biasing force to the bone screw; and/or the securing step may include rotating the assembly cap in a first direction to threadably engage a threading defined on an outer surface of the assembly cap with a threading defined on an inner surface of the housing; and/or the inserting step may include allowing the retaining ring to expand to an expanded state as the head of the bone screw is received within the lumen of the retaining ring and, thereafter, allowing the retaining ring to return to an unexpanded state after the head of the bone screw has passed through the lumen; and/or the method may further include installing a spinal rod within a U-shaped slot defined through an outer surface of the housing and extending through the proximal surface thereof; and/or the method may further include rotating a set screw in a first direction to threadably engage a threading defined on an outer surface of the set screw with a corresponding threading defined on an inner surface of the housing, whereby rotation of the set screw in the first direction may cause the set screw to move in a distal direction which, in turn, may cause a corresponding distal movement of the spinal rod, the anvil, and the retaining ring; and/or the corresponding distal movement of the retaining ring may translate the retaining ring from the first portion of the assembly cap to the second portion of the assembly cap and may cause the retaining ring to transition from the first configuration to the second configuration and may fix a rotational and angular position of the bone screw relative to the modular head assembly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal fixation device, comprising:
a bone screw including a head and a shank extending from the head;
a modular head assembly, comprising:
a housing having a proximal surface, a distal surface, and a throughhole formed through the housing from the proximal surface to the distal surface;
an anvil slidable within a portion of the throughhole;
a biasing member circumferentially surrounding the anvil to impart a distally directed force on the head of the bone screw;
an assembly cap secured to the housing, the assembly cap including an inner surface defining a cavity having a first portion and a second portion, the first portion having a first diameter and the second portion having a second diameter smaller than the first diameter, the anvil located entirely above the assembly cap;
a retaining ring positioned at least partially within the cavity of the assembly cap, the retaining ring transitionable between a first configuration in which the retaining ring is sized to receive the head of the bone screw and a second configuration in which the retaining ring is compressed about the bone screw,
wherein movement of the retaining ring from the first portion to the second portion compresses the retaining ring from the first configuration to the second configuration and secures the bone screw relative to the housing.

2. The spinal fixation device of claim 1, wherein a distal portion of the housing defines a counterbore terminating at an annular face.

3. The spinal fixation device of claim 2, wherein an inner surface of the housing defines at least one slot.

4. The spinal fixation device of claim 3, wherein the anvil defines a proximal end, a distal end and a circumferential sidewall extending therebetween, the circumferential sidewall including at least one outwardly extending lug arranged to be slidably received within the at least one slot.

5. The spinal fixation device of claim 4, wherein the at least one lug comprises two lugs diametrically opposed from one another about the circumferential sidewall of the anvil.

6. The spinal fixation device of claim 4, wherein distal end of the anvil comprises an outwardly extending flange.

7. The spinal fixation device of claim 6, wherein the biasing member is provided between the outwardly extending flange and the at least one outwardly extending lug.

8. The spinal fixation device of claim 7, wherein the biasing member is biased between the outwardly extending flange of the anvil and the annular face of the counterbore.

9. The spinal fixation device according to claim 7, wherein the biasing member is a wave spring.

10. The spinal fixation device of claim 2, wherein the counterbore defines an internal threading and the assembly cap includes an external threading configured to threadably engage the internal threading of the counterbore.

11. The spinal fixation device of claim 1, wherein the retaining ring defines a proximal end and a distal end, the proximal and distal ends defining a lumen therethrough.

12. The spinal fixation device of claim 11, wherein the retaining ring is formed from a resilient material, and wherein an outer surface of the retaining ring defines a slit in communication with the lumen.

13. The spinal fixation device of claim 11, wherein the proximal end of the retaining ring defines an outwardly extending shelf arranged to contact the anvil.

14. The spinal fixation device of claim 1, wherein the inner surface of the assembly cap includes an inwardly extending ledge at a distal end of the assembly cap to limit distal movement of the retaining ring.

15. A method of assembling a spinal fixation device, comprising:
providing a modular head assembly, the modular head assembly including a housing having a throughhole formed through the housing from a proximal surface of the housing to a distal surface of the housing, an anvil slidable within a portion of the throughhole, a biasing member circumferentially surrounding the anvil, an assembly cap secured to the housing including an inner surface defining a cavity having a first portion with a first diameter and a second portion with a second diameter smaller than the first diameter, and a retaining ring positioned at least partially within the cavity of the assembly cap and transitionable between a first configuration in which the retaining ring is sized to receive a head of a bone screw and a second configuration in which the retaining ring is compressed about the bone screw, the anvil located entirely above the assembly cap;
securing the bone screw within bone;
positioning a bore defined through a distal surface of the assembly cap adjacent the head of the bone screw;

advancing the modular head assembly over the head of the bone screw such that the head of the bone screw is received within the bore;

moving the retaining ring from the second portion of the cavity to the first portion of the cavity;

inserting the head of the bone screw through a lumen defined through distal and proximal surfaces of the retaining ring; and allowing the biasing member to apply a distally directed biasing force to the anvil which, in turn, applies a biasing force to the bone screw.

16. The method of claim 15, wherein the securing step comprises rotating the assembly cap in a first direction to threadably engage a threading defined on an outer surface of the assembly cap with a threading defined on an inner surface of the housing.

17. The method according to claim 15, wherein the inserting step comprises allowing the retaining ring to expand to an expanded state as the head of the bone screw is received within the lumen of the retaining ring and, thereafter, allowing the retaining ring to return to an unexpanded state after the head of the bone screw has passed through the lumen.

18. The method according to claim 15, further comprising installing a spinal rod within a U-shaped slot defined through an outer surface of the housing and extending through the proximal surface thereof.

19. The method according to claim 18, further comprising rotating a set screw in a first direction to threadably engage a threading defined on an outer surface of the set screw with a corresponding threading defined on an inner surface of the housing, wherein rotation of the set screw in the first direction causes the set screw to move in a distal direction which, in turn, causes a corresponding distal movement of the spinal rod, the anvil, and the retaining ring.

20. The method according to claim 19, wherein the corresponding distal movement of the retaining ring translates the retaining ring from the first portion of the assembly cap to the second portion of the assembly cap and causes the retaining ring to transition from the first configuration to the second configuration and fix a rotational and angular position of the bone screw relative to the modular head assembly.

* * * * *